United States Patent [19]
Fournier et al.

[11] Patent Number: 5,972,705
[45] Date of Patent: Oct. 26, 1999

[54] SEQUENCE-SPECIFIC METHYLATION OF RIBONUCLEIC ACID

[75] Inventors: Maurille J. Fournier; Jingwei Ni, both of Amherst, Mass.

[73] Assignee: University of Massachusetts, Boston, Mass.

[21] Appl. No.: 08/883,920

[22] Filed: Jun. 27, 1997

Related U.S. Application Data

[60] Provisional application No. 60/020,842, Jun. 28, 1996.
[51] Int. Cl.[6] .......................... C07H 21/02; C12P 19/34; A01N 43/04
[52] U.S. Cl. ..................... 435/440; 435/91.1; 435/445; 514/44; 536/23.1
[58] Field of Search ................... 435/91.1, 442, 435/440, 455; 536/23.1; 514/44

[56] References Cited

PUBLICATIONS

Bachellerie et al., "Antisense snoRNAs: a family of nucleolar RNAs with long complementarities to rRNA", *Elsevier Trends Journals* 20:261–264, 1995.

Caffarelli, et al., "Processing of the Intro–Encoded U16 and U18 snoRNAs: The Conserved C and D Boxes Conrol Both the Processing . . . of the Mature snoRNA", *The EMBO Journal*, 15(5):1121–1131, 1996.

Cavaillé et al., "Targeted ribose methylation of RNA in vivo directed by tailored antisense RNA guides", *Nature* 383:732–735, 1996.

Eichler et al., "Isolation and Characterization of a Nucleolar 2'–0–Methyltransferase from Ehrlich Ascites Tumor cells", *Biochemistry* 26:1639–1644, 1987.

Kiss–László, et al., "Site–Specific Sugar Methylation of rRNA: A novel function for small nuclear RNAs", Abstract RNA '96, The First Annual Meeting of the RNA Society, May 28 to Jun. 2, 1996, Madison, Wisconsin.

Kiss–Lászloó, et al., "Site–Specific Ribose Methylation of Preribosomal RNA: A Novel Function for Small Nucleolar RNAs", *Cell* 85:1077–1088, 1996.

Nicoloso et al., "Intron–encoded Antisense Small Nucleolar RNAs: The Characterization of Nine Novel Species Points to Their Direct Role as Guides for the 2'–0–ribose Methylation of rRNAs", *J. Mol. Biol* 260, 178–195, 1996.

Maxwell et al., "The Small Nucleolar RNAs", *Ann. Rev. Biochem* 35:897–934, 1995.

Segal et al., "A Nucleolar 2'–0–Methyltransferasse", *The Journal of Biological Chemistry* 266(36): 24385–24389, 1991.

Tycowski et al., "A small nucleolar RNA requirement for site–specific ribose methylation of rRNA in Xenopus", *Proc. Natl. Acad. Sci. USA* 93:14480–14485, 1996.

Yu et al., "A new method for detecting sites of 2'0–methylation in RNA molecules", *RNA* 3:324–331, 1997.

*Primary Examiner*—Bradley L. Sisson
*Assistant Examiner*—Einar Stole
*Attorney, Agent, or Firm*—Fish & Richardson P.C.

[57] ABSTRACT

The invention features nucleic acid molecules and methods for use in site-specific methylation of ribonucleotides. The methods of the invention can be used to modulate RNA folding, RNA processing, RNA cleavage, and other processes involving sequence-specific recognition of RNA sequences, as well as for promoting RNA stability.

34 Claims, 2 Drawing Sheets

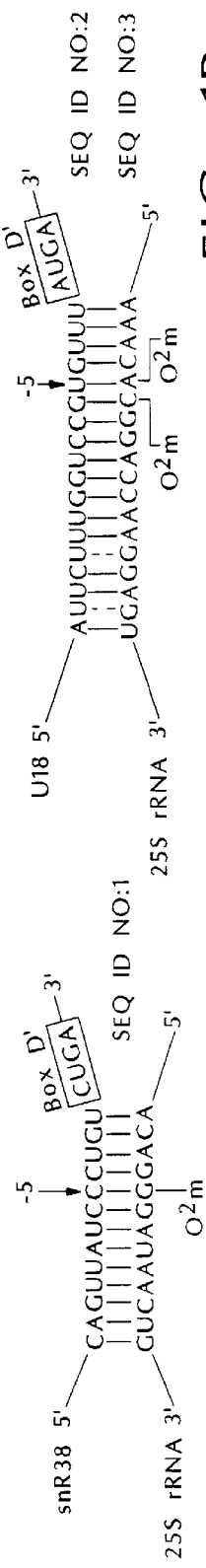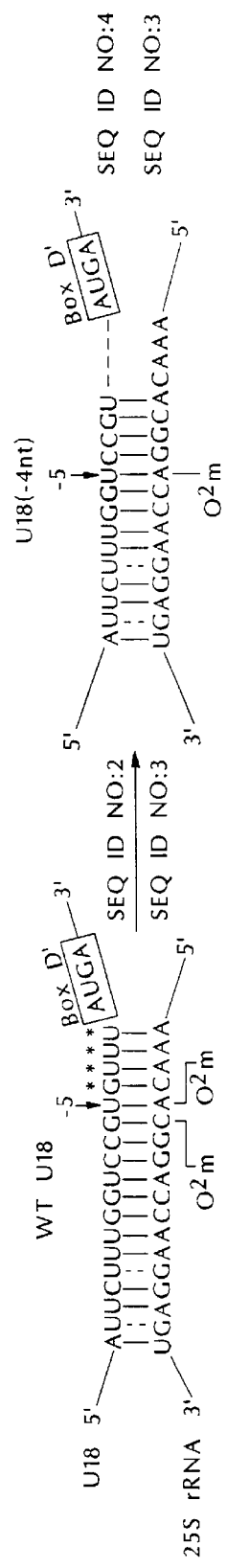
FIG. 1A   FIG. 1B   FIG. 2

```
                        SEQUENCE LISTING

<160> NUMBER OF SEQ ID NOS: 9

<210> SEQ ID NO 1
    <211> LENGTH: 17
    <212> TYPE: RNA
    <213> ORGANISM: Yeast snR38

<400> SEQUENCE: 1
caguuauccc ugucuga                                              17

<210> SEQ ID NO 2
    <211> LENGTH: 22
    <212> TYPE: RNA
    <213> ORGANISM: Yeast U18

<400> SEQUENCE: 2
auucuuuggu ccguguuuau ga                                        22

<210> SEQ ID NO 3
    <211> LENGTH: 18
    <212> TYPE: RNA
    <213> ORGANISM: Yeast 25S

<400> SEQUENCE: 3
aaacacggac caaggagu                                             18

<210> SEQ ID NO 4
    <211> LENGTH: 18
    <212> TYPE: RNA
    <213> ORGANISM: Yeast U18

<400> SEQUENCE: 4
auucuuuggu ccguauga                                             18

<210> SEQ ID NO 5
    <211> LENGTH: 17
    <212> TYPE: RNA
    <213> ORGANISM: Yeast snR38 and U18

<400> SEQUENCE: 5
uugguccgug uuucuga                                              17

<210> SEQ ID NO 6
    <211> LENGTH: 13
    <212> TYPE: RNA
    <213> ORGANISM: Yeast 18S
```

```
<400> SEQUENCE: 6
ggugaaccug cgg                                                          13

<210> SEQ ID NO 7
<211> LENGTH: 13
<212> TYPE: RNA
<213> ORGANISM: Yeast 18S

<400> SEQUENCE: 7
augcugaaaa uca                                                          13

<210> SEQ ID NO 8
<211> LENGTH: 13
<212> TYPE: RNA
<213> ORGANISM: Yeast snR38

<400> SEQUENCE: 8
acagggauaa cug                                                          13

<210> SEQ ID NO 9
<211> LENGTH: 13
<212> TYPE: RNA
<213> ORGANISM: Yeast smR38 and U18

<400> SEQUENCE: 9
aaacacggac caa                                                          13
```

SEQUENCE-SPECIFIC METHYLATION OF RIBONUCLEIC ACID

This application claims priority from U.S. Provisional Application No. 60/020,842, filed on Jun. 28, 1996.

This invention was supported in part by the U.S. Government under United States Public Health Service, National Institutes of Health grant GM 19351. The Government has certain rights in the invention.

BACKGROUND OF THE INVENTION

This invention relates to nucleic acid molecules and methods for sequence-specific methylation of ribonucleic acid.

Ribosomes are large, complex particles that play a central role in protein synthesis. Ribosomes are produced in a discrete region of the cell nucleus, designated the nucleolus. Eukaryotic ribosomes consist of 40S and 60S subunits, which each contain multiple ribonucleic acid (RNA) and protein components. For example, the 40S ribosomal subunit contains 18S ribosomal RNA (rRNA) and the 60S ribosomal subunit contains 5S, 28S (28S in metazoans and 25S in unicellular eukaryotes, such as yeast), and 5.8S rRNAs. Each of the rRNAs, except 5S rRNA, are transcribed in the nucleolus as segments of a large precursor RNA, which is cleaved in the production of the mature rRNAs. Additional rRNA processing events include modification of certain bases by, e.g., conversion of uridine to pseudo-uridine or methylation of ribose 2'-hydroxyl groups.

In addition to rRNAs, eukaryotic nucleoli contain complex populations of small nucleolar RNAs (snoRNAs), several of which have been shown to be required for rRNA processing (Maxwell et al., Annu. Rev. Biochem. 35:899, 1995; Filipowicz et al., Mol. Biol. Rep. 18:235, 1993; Fournier et al., Trends Biochem. Sci. 18:131, 1993; Sollner-Webb, Cell 75:403, 1993). snoRNAs associate with multiple proteins to form small nucleolar ribonucleoprotein (snoRNP) particles. For example, nearly all snoRNAs are associated with the nucleolar protein fibrillarin, which itself is required for normal processing and methylation of rRNA.

Some snoRNAs are encoded within the introns of genes, e.g., genes coding for proteins involved in ribosome synthesis and function. These snoRNAs contain conserved sequence motifs, and several of them also contain regions of sequence complementarity to conserved regions of rRNA of up to 21 nucleotides. In several cases, methylated nucleotides are present in the rRNA sequence elements that are complementary to these snoRNAs (Bachellerie et al., Trends Biochem. Sci. 20:261, 1995).

SUMMARY OF THE INVENTION

The invention provides nucleic acid molecules and methods for use in site-specific methylation of ribonucleotides, such as ribonucleotides in RNA molecules. The methods of the invention can be used to modulate RNA folding, RNA processing (e.g., the RNA cleavage and ligation events involved in, e.g., pre-mRNA splicing), RNA cleavage, and other processes involving sequence-specific recognition of RNA sequences (e.g., translation), as well as for promoting RNA stability.

Accordingly, in one aspect, the invention features a method of methylating the 2'-O-hydroxyl group of a target ribonucleotide (e.g., a ribonucleotide that is in an RNA cleavage site) in a target nucleic acid. In this method, the target nucleic acid is contacted with a modified snoRNA under conditions sufficient for methylation of the target ribonucleotide to occur (e.g., in a cell or in nuclear extracts). The target nucleic acid (e.g., RNA, such as mRNA, or the genome of a pathogen, or RNA transcribed from the genome of a pathogen) can be in a cell, for example, in a nucleolus, a nucleus, cytoplasm, or a mitochondrion of a cell.

The modified snoRNA used in this method contains (1) a binding nucleotide sequence that hybridizes to a portion of a target nucleic acid (e.g., RNA, such as mRNA, or the genome of a pathogen, or RNA transcribed from the genome of a pathogen such as a pathogenic fungus or a virus, e.g., human immunodeficiency virus; or a DNA-RNA hybrid molecule) including a target ribonucleotide (e.g., a ribonucleotide that is in an RNA cleavage site), and (2) a D box sequence located five nucleotides downstream (3') from a nucleotide in the binding nucleotide sequence that pairs with the target ribonucleotide. The modified snoRNA targets methylation of the target ribonucleotide in the target nucleic acid. The modified snoRNA can be essentially identical to naturally occurring snoRNAs, only differing in the sequence of the targeting region. Alternatively, a snoRNA analog, including elements required for targeted methylation, but not other snoRNAs features, can be used.

The D box is a conserved sequence of nucleotides in snoRNAs and can consist of a sequence selected from, e.g., 5'-CUGA-3', 5'-AUGA-3', 5'-CCGA-3', 5'-CAGA-3', 5'-CUUA-3', 5'-UUGG-3', and 5'-CAGC-3'.

The binding nucleotide sequence preferably hybridizes with at least ten (e.g., 12, or 13–22) nucleotides of the target nucleic acid, but can also hybridize with fewer than 10 consecutive nucleotides in the target nucleic acid under suitable conditions. Of course, the region of hybridization can contain gaps, provided that a sufficient basepairing interaction is maintained to permit ribonucleotide-specific methylation. Permissible variations in the level of sequence complementarity can readily be determined by one skilled in the art.

In the methods of the invention, hybridization of the binding nucleotide sequence to the portion of the target nucleic acid including the target ribonucleotide results in methylation of the target ribonucleotide.

In a second aspect, the invention features the modified snoRNA itself.

The invention provides several advantages, as it permits site-specific methylation of ribonucleotides. Methylation of specific ribonucleotides in, e.g., RNA molecules, can be used to modulate a wide variety of biological processes. For example, RNA stability, folding, processing, cleavage, and recognition can be modulated by such methylation. Accordingly, the new methods can be used, e.g., to stabilize therapeutic antisense RNAs and ribozymes. In addition, the methods of the invention can be used to modulate gene expression. For example, methylation of RNA nucleotides can be carried out to, e.g., block pre-mRNA splicing, RNA poly-adenylation, RNA capping, RNA 3'-end formation, or translation of mRNA.

Thus, the new methods can be used to reduce growth rates in cells. To achieve that, a modified snoRNA of the invention, which is designed to hybridize to a portion of a target nucleic acid within the cells, is introduced into the cells (e.g., tumor or fungal cells); the snoRNA methylates a target RNA involved in cell growth (such as rRNA, or mRNA of oncogenic genes such as ras, met, sis, erbB, abl, jun, fos, or myc), thereby inhibiting growth of the cells.

The new methods can also be used to inhibit viral replication in cells. To do so, a modified snoRNA of the invention is allowed to contact the viral target nucleic acid, e.g., by being introduced into a viral-infected cell. The modified snoRNA is designed such that its binding nucleotide sequence hybridizes to (e.g., is complementary to) a viral sequence that is involved in viral replication.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, some suitable methods and materials are described below. All publications, patent applications, patents, and other references mentioned herein are incorporated by reference in their entirety. In case of a conflict, the present specification will control. In addition, the described materials, methods, and examples are illustrative only and are not intended to be limiting.

Other features and advantages of the invention will be apparent from the following detailed description and the claims.

BRIEF DESCRIPTION OF THE DRAWINGS

FIG. 1A is a schematic representation of the basepairing interaction between snR38 (SEQ ID NO:1), which is a snoRNA in *Saccharomyces cerevisiae*, and 25S rRNA of *S. cerevisiae* (SEQ ID NO:8).

FIG. 1B is a schematic representation of the basepairing interaction between U18 (SEQ ID NO:2), which is a snoRNA in *S. cerevisiae*, and 25S rRNA of *S. cerevisiae* (SEQ ID NO:3).

FIG. 2 is a schematic representation showing the movement of Box D' in U18 for generating U18(-4nt) (SEQ ID NO:4). Box D is a conserved sequence motif in snoRNAs, generally consisting of the nucleotide sequence 5'-CUGA-3', or a variant thereof (see below). A second Box D sequence occurring in a snoRNA is designated as "Box D'." In the case of U18, Box D' consists of the sequence 5'-CUGA-3'.

DETAILED DESCRIPTION

Figure 3:
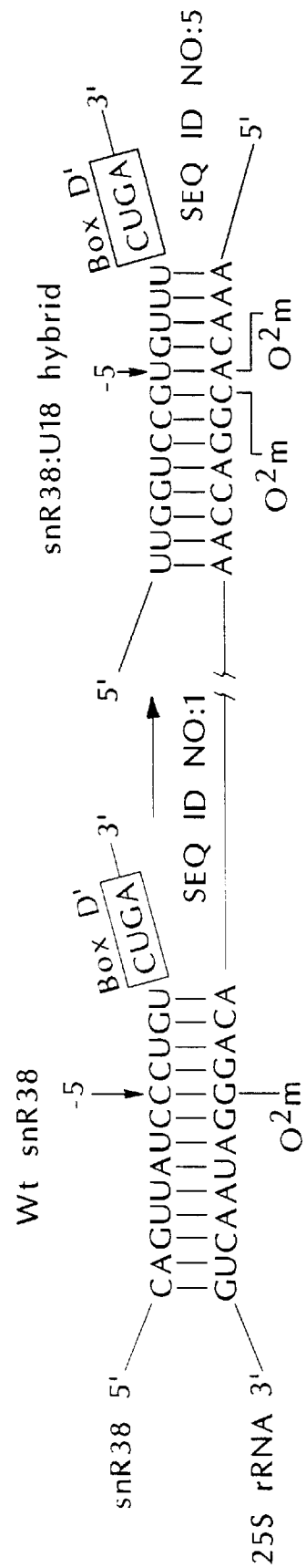
FIG. 3 is a schematic representation of the basepairing interactions between 25S rRNA (SEQ ID NO:9) and (1) snR38, and (2) a snR38: U18 hybrid, consisting of snR38 containing a U18 antisense element (SEQ ID NO:5).

The invention provides nucleic acid molecules and methods for use in site-specific methylation of 2'-hydroxyl groups of specific ribonucleotides in RNA molecules.

As shown in the experiments described below, methylation of rRNA nucleotides in eukaryotic cells depends on the presence of specific snoRNAs, which contain nucleotide sequences that are complementary to the region (or portion) in the rRNA adjacent to the ribonucleotide to be methylated. More specifically, the rRNA nucleotide to be methylated is paired with a snoRNA nucleotide that is five nucleotides upstream from a conserved snoRNA element located immediately, or one nucleotide, 3' to the snoRNA sequence complementary to the rRNA (see, e.g., FIGS. 1A and 1B). The conserved snoRNA element can also be located more than 5 nucleotides away, but brought into the same effective proximity with the target rRNA nucleotide during three-dimensional interaction of the snoRNA and the rRNA.

The conserved snoRNA element is known as box D or box D', and typically consists of the sequence: 5'-CUGA-3', but variants of this sequence, such as 5'-AUGA-3', 5'-CCGA-3', 5'-CAGA-3', 5'-CUUA-3', 5'-UUGG-3', and 5'-CAGC-3', are also useful. Active variants of the canonical sequence (i.e., 5'-CUGA-3') can be identified by using the methods described herein.

Shifting the location of the box D/D' element, relative to the snoRNA nucleotide paired with the ribonucleotide to be methylated, by a certain number of nucleotides results in a change of the methylation site by the same number of nucleotides, in the same direction (see below and FIG. 2). This observation shows that the box D/D' element is used in selection of the methylation site. In addition, substituting the rRNA complementary sequence of a first snoRNA with that of a second snoRNA results in targeting of the natural rRNA target of the second snoRNA (see below and FIG. 3).

These observations show that snoRNAs can be modified to direct methylation of novel, specific target ribonucleotides by replacing wild type snoRNA sequences that are complementary to rRNA sequences with sequences complementary to regions surrounding the novel, specific target ribonucleotides. Such modified snoRNAs can be made using standard methods, such as recombinant PCR (see, e.g., Chen et al., BioTechniques 17:657, 1994; Innis et al. (eds.), *PCR Protocols: A Guide to Methods and Applications*, Academic Press, Inc., San Diego, Calif., 1990). This method can be carried out, for example, as follows. A first PCR reaction is carried out using (1) a first primer complementary to one end of a first strand of DNA corresponding to the snoRNA to be modified, (2) a second primer containing 5' and 3' sequences that are complementary to regions in the second strand of the DNA and that flank the sequence to be modified, and internal sequences corresponding to the novel sequence to be substituted into the snoRNA, and (3) DNA corresponding to the snoRNA to be modified as the template. A second PCR reaction is carried out using (1) a third primer complementary to the second strand of the DNA at the opposite end from the first primer, and (2) a fourth primer containing 5' and 3' sequences that are complementary to regions in the first strand of the DNA and that flank the sequence to be modified, and internal sequences corresponding to the novel sequence to be substituted into the snoRNA, and (3) DNA corresponding to the snoRNA to be modified as the template. A mixture of the denatured and renatured products of the first and second PCR reactions is used as the template for a third PCR reaction, using the first and the third primers as the primers. This third reaction yields a PCR product encoding a snoRNA containing the desired modification. This DNA can be transcribed into the modified snoRNA, which can be used in methods to methylate novel, targeted sites, as described further below.

Any snoRNA that normally methylates a specific rRNA nucleotide can be modified to methylate novel nucleotides in other RNAs in the methods of the invention. For example, human snoRNAs such as U18, U20, U24, U21, and U13 can be used (see, e.g., Bachellerie et al., supra; Maxwell et al., Ann. Rev. Biochem. 35:897, 1995; and references therein.) snoRNAs from other species, such as mouse, hamster, chicken, frog, and yeast, can also be used.

Any ribonucleotide that can be positioned in the appropriate context of a basepairing interaction with a modified snoRNA can be methylated using the methods of the invention. Such a ribonucleotide can be present in RNA, e.g., rRNA, snoRNA, transfer RNA (tRNA), decoy RNAs, small RNA components of the pre-mRNA splicing apparatus (snRNAs), signal recognition particle (SRP), the RNaseP complex, mitochondrial RNA, or chloroplast RNA. The ribonucleotide can be one that is already modified at a position other than the 2'-O-hydroxyl group of its ribose, e.g., at a position in its base. In addition, the ribonucleotide can be in the context of a molecule containing, e.g., ribonucleotides and deoxyribonucleotides.

In addition to naturally occurring RNAs, the new methods can be used to modify RNAs transcribed from altered genes, such as genes containing mutations, e.g., point mutations or chromosomal transversions. The methods can also be used to methylate RNA that is present in a cell as a result of an infection, such as a bacterial or viral infection. For example, it may be desirable to impede the expression and/or replication of such pathogen-derived RNAs (see below). As a specific example, the methods of the invention can be used to affect steps of viral RNA maturation that involve RNA cleavage.

The methods of the invention can also be used to methylate RNA that is present in a cell as a result of gene therapy. For example, RNAs produced by transcription of genes that (1) were introduced into cells by gene therapy and (2) encode therapeutic proteins, ribozymes, or antisense RNAs can be stabilized by such methylation.

The presence of 2'-O-methyl groups in an RNA molecule alters its chemical properties, and thus affects the biological activity of the RNA. Biological functions that can be altered by 2'-O-methylation include, for example, folding of the RNA, as well as interaction of the RNA with other molecules, including other RNAs, DNA, proteins, other classes of cellular molecules and components, and non-biological materials.

Applications of this technology include, for example, altering the biological and chemical stability of an RNA in a cell or in vitro. Methylation of the 2'-hydroxyl group blocks base-mediated hydrolysis of the internucleotide phosphodiester bond, as a free 2'-hydroxyl moiety is needed for formation of the required 2'-3'-cyclic intermediate. 2'-O-methylation also provides stability against cleavage by nucleolytic enzymes and alkaline hydrolysis, both in vivo and in vitro. Enhanced stability to hydrolysis is an important property for many in vivo and in vitro applications involving RNA.

In addition to stabilizing targeted RNAs, snoRNA-directed 2'-O-methylation can be used to impair the expression of RNAs. For example, 2'-O-methylation can be used to block site-specific RNA cleavage reactions involving the affected internucleotide bond. This will impair cleavage reactions involved in, for example, the maturation of precursor RNA molecules, including, e.g., natural and unnatural precursor forms of rRNA, snoRNA, snRNA, MRNA, tRNA, and RNAs from pathogens, such as viruses. Other post-transcriptional maturation reactions that can be affected by 2'-O-methylation include the addition of 5' terminal cap structures, formation of 3' poly-A tails, editing of RNA sequences, formation of modified nucleotides, and formation of non-canonical 5', 3' internucleotide bonds.

As a specific example of 2'-O-methylation affecting gene expression, nucleotides at the 5' and/or 3' splice sites of a pre-mRNA can be methylated to block cleavage, and thus pre-mRNA splicing and production of a mature mRNA. This can be used to block the production of undesirable proteins in cells, for example, proteins required for the replication or assembly of a viral pathogen.

Recognition of RNA by proteins, e.g., in the formation of RNA:protein complexes, can also be affected by methylation of RNA nucleotides using the methods of the invention. For example, methylation of the ribosome binding site and other sites recognized by the translation machinery (e.g., translation factors and tRNA) can be used to disrupt translation. Methylation can also disrupt replication of RNAs by RNA-dependent DNA polymerases and RNA replicases. Post-synthesis maturation and packaging of RNA molecules, which is another important feature in the replication of many pathogens, e.g., viruses, can also be compromised by methylation of RNA nucleotides.

Many RNAs function by forming complex secondary and higher order structures. 2'-O-methylation of nucleotides in such an RNA can alter its ability to fold properly to form such structures. Accordingly, the functions of such RNAs can be affected using the methods of the invention.

snoRNA-directed methylation can also be carried out in cell-free conditions. Such methods can include modification of natural or artificial RNAs in extracts from cells or reactions that contain few or no natural biological molecules. Methylation in the latter case would be effected by biological mimicry, using reaction components that feature or are based on elements of the natural biological machinery.

Nuclear extracts, such as fractionated nuclear extracts, which are prepared using standard methods, can be used to carry out in vitro methylation by modified snoRNAs. Of course, the utility of such extracts depends on their containing snoRNP protein components that may be required for methylation. In addition, a methyltransferase may be required.

Example—Modification of Splice Sites of HIV pre-mRNA

Expression of HIV-1 genes involves the splicing of a large, single mRNA precursor, which leads to the production of mRNAs falling into three classes: unspliced RNA (genomic RNA), singly-spliced RNAs (e.g., env), and multiply spliced RNAs (e.g., vpr, rev, and nef). Each of the spliced classes includes several mRNA species specifically encoding one or two HIV-1 proteins.

HIV-1 infection in a patient can be treated by inhibiting splicing of the HIV-1 precursor RNA, as inhibiting this process will prevent, e.g., the production of proteins required for HIV reproduction. The methods of the invention can be used for inhibiting splicing of HIV-1 precursor RNA. For example, the rRNA binding sequence of a snoRNA can be replaced with a sequence that hybridizes to an HIV-1 sequence that includes a splice site. The modified snoRNA can be designed so that hybridization of the snoRNA with the HIV-1 precursor RNA places the relevant splice site nucleotide so that it is paired with the modified snoRNA nucleotide, that is 5 nucleotides upstream from the D(D') box.

Modified snoRNAs directed against HIV-1 splice sites can be tested in appropriate cell culture and animal model systems, which are well known to those skilled in the art. For example, a syncytium inhibition assay can be carried out. This assay method is adapted from methods previously described by Hildreth et al., Science 244:1075, 1989. Briefly, 1 ml of HIV-1RF virus stock ($2 \times 10^7$ virus particles/ml) is mixed with $5 \times 10^5$ CEMss (syncytia sensitive) cells in the presence or absence of a snoRNA targeted to, e.g., an HIV splice site, in 2.0 ml of growth medium. The mixture is incubated at 37° C. for 24 hours, and the syncytia formation of the cells is observed under a microscope and recorded.

In addition, these modified snoRNAs can be used in the methods described below for introducing modified snoRNAs into cells, which methods can be used for treating patients infected with HIV-1.

Experimental Results

The following experiments were carried out using the yeast S. cerevisiae.

Antisense snoRNAs Provide Sequence Specificity for the Formation of 2'-O-methylated Nucleotides in rRNA Eight snoRNAs containing sequences complementary to ribosomal RNA ("rRNA") were found to be required for the synthesis of 2'-O-methylated nucleotides within the corresponding complementary segments of rRNA. The requirement was demonstrated by analysis of rRNA prepared from cells lacking the individual test snoRNAs (see, e.g., Jarmolowski et al., EMBO J. 13:4503, 1990).

The rRNA was analyzed using a standard primer extension assay in which a base modification (i.e., 2'-O-methylation) is detected as a nucleotide-concentration-dependent pause in the primer extension reaction (see, e.g., Maden et al., Biochimie 77:22, 1995). (The primer extension method of Sirum-Connolly et al., Science 262:1886, 1993, may also be used to detect the presence of ribose methylation, and involves partial alkaline digestion of the RNA being assayed.) Briefly, primer extension was performed at four different dNTP concentrations, using the rRNA as a template. Transcripts generated by the primer extension were size-fractionated on a polyacrylamide gel. The presence of a methylated ribonucleotide in the rRNA was indicated by a transcript whose transcription terminates at that ribonucleotide.

The base-pairing interactions of two snoRNAs, snR38 and U18, with their respective target sequences are schematically shown in FIGS. 1A and 1B. To study the role of these two snoRNAs in rRNA methylation, rRNA samples were prepared from wild-type cells (WT), cells with disrupted chromosomal genes for snR38 (or U18), and cells with inactive chromosomal snR38 (or U18), but transformed with plasmid-encoded snR38 (or U18) (Li et al., Mol. Cell. Biol. 10:1145, 1990; Jarmolowski et al., supra). Unmodified 25S rRNA produced by in vitro transcription was used as a negative control. Primer extension assays showed that methylation of G at position 2811 of 25S rRNA was abolished in cells lacking snR38; however, the methylation was restored after a snR38-encoding plasmid was introduced into the mutated cells. Similarly, methylation of A at position 648 (and C at position 649) of 25S rRNA was abolished in cells lacking U18, and the methylation was restored after a U18-encoding plasmid was introduced into the mutated cells.

In addition to snR38 and U18 (GenBank accession no. U12981), methylation of 25S rRNA was also shown to be blocked in yeast cells lacking snoRNA species snR39 (GenBank accession no. U26011), snR40 (GenBank accession no. U26015), snR47 (GenBank accession no. U56648), or U24 (GenBank accession no. 248760). Methylation of 18S rRNA was blocked in yeast cells lacking snR41 (GenBank accession no. U26016), or U14 (GenBank accession no. M21124).

For each snoRNA, the modification effected is located at a constant position relative to the D(D') box of the snoRNA. The ribonucleotide in this position is paired with a snoRNA nucleotide located five nucleotides upstream from a short conserved sequence known as Box D or D' (see, e.g., FIGS. 1A and 1B). The Box D(D') element occurs at the 3' end of the antisense sequence of the snoRNA. Box D(D') has been found in over ten complementary snoRNAs in yeast and in most complementary snoRNAs in vertebrates, and has thus far always been observed to be 5-nucleotides from a 2'-O-methylated nucleotide, where these are known. These observations show that the snoRNA provides a docking and targeting function for methylation.

More direct evidence of the targeting role of snoRNAs was obtained by two additional experiments.

In one experiment, the site of rRNA modification was shifted by four nucleotides, by moving the box D' element of U18 four nucleotides upstream (FIG. 2). Samples of rRNA were prepared from wild-type cells (WT), cells containing a disrupted chromosomal U18 gene (−U18), cells containing a disrupted chromosomal U18 snoRNA gene, but transformed with a plasmid containing a wild-type U18 gene or a plasmid containing a U18 gene allele with a 4 nucleotide deletion upstream of Box D' (U18-4nt). Unmodified rRNA produced by in vitro transcription was used as a negative control. Primer extension assays were performed to detect methylation of rRNA target sequences.

In the second experiment, the specificity of a snoRNA was changed by replacing the targeting sequence with one from a different snoRNA (see, e.g., Chen et al., BioTechniques 17:657, 1994). The 25S rRNA-complementary sequence in snR38 was replaced with that from U18 (FIG. 3), and modification at the U18 target site was restored in cells lacking wild-type U18. Methylation patterns were determined, by primer extension assays, for 25S rRNA from wild-type cells (WT), cells with a disrupted chromosomal U18 gene (−U18), cells with an inactive chromosomal U18 gene, but containing a plasmid with a U18 gene (+U18), cells with an inactive chromosomal U18 gene, but containing a plasmid that encodes snR38 with the U18 antisense element (snR38: U18), and cells with an inactive chromosomal U18 gene, but containing two plasmids that encode the hybrid snR38: U18 gene (snR38: U18) and wild-type snR38 snoRNA (+snR38). These results show that (1) the site of modification is determined by the position of box D', and (2) snoRNA targeting elements can be exchanged.

Similar experiments were also performed for 18S rRNA in yeast cells that lack their endogenous snR38. In these experiments, the 25S rRNA-complementary sequence in snR38 was replaced by a sequence complementary to a region of 18S rRNA that contains A1779 (5'-GGUGaACCUGCGG-3', i.e, SEQ ID NO:6; A1779 is in lower case) or U1757 (5'-AUGCuGAAAAUCA-3', i.e., SEQ ID NO:7; U1757 is in lower case). These two positions normally are not methylated at the 2'-O-hydroxyl group, but became so when the cells expressed the mutated snR38 with the corresponding new guide sequence. A1779 was also methylated at its adenine.

Notably, introduction of a methyl group at A1779 or U1757 retarded cell growth. Colony size of cells with methylated A1779 was about one tenth of that of wild type cells, whereas colonies of cells with methylated U1757 were barely visible 3–4 days after plating. In these experiments, cells were grown on agarose plates selective for uracil, a marker of the snoRNA-encoding plasmids.

Use

The modified snoRNAs of the invention, which can be used in methods to methylate novel, specific ribonucleotides, can be introduced into cells using standard gene therapy methods. For example, the snoRNAs of the invention can be produced within a target cell by transcription of a nucleic acid molecule containing a promoter sequence operably linked to a sequence encoding the modified snoRNA. In this method, the nucleic acid molecule is contained within a non-replicating linear or circular DNA or RNA molecule, is contained within an autonomously replicating plasmid or viral vector, or is integrated into the host genome. Any vector that can transfect a target cell can be used in the invention. Preferred vectors are viral vectors, including those derived from retroviruses (see, e.g., WO89/07136; Rosenberg et al., N. Eng. J. Med. 323(9):570–578, 1990), adenovirus (see, e.g., Morsey et al., J. Cell. Biochem., Supp. 17E, 1993; Graham et al., in Murray, ed., *Methods in Molecular Biology: Gene Transfer and Expression Protocols*, Vol. 7, Clifton, N.J., the Human Press 1991:

109–128), adeno-associated virus (Kotin et al., Proc. Natl. Acad. Sci. USA 87:2211–2215, 1990), replication defective herpes simplex viruses (HSV; Lu et al., Abstract, page 66, Abstracts of the Meeting on Gene Therapy, Sep. 22–26, 1992, Cold Spring Harbor Laboratory, Cold Spring Harbor, N.Y.), replication-defective hepatitis viruses (e.g., HBV and HCV), and any modified versions of these vectors. Methods for constructing expression vectors are well known in the art (see, e.g., *Molecular Cloning: A Laboratory Manual*, Sambrook et al., eds., Cold Spring Harbor Laboratory, 2nd Edition, Cold Spring Harbor, N.Y., 1989).

Appropriate regulatory sequences (e.g., promoters and enhancers) can be inserted into such vectors using methods known to those skilled in the art, for example, by homologous recombination (Graham et al., J. Gen. Virol. 36:59–72, 1977), or other appropriate methods (see, e.g., Sambrook et al., supra). Promoters are inserted into the vectors so that they are operably linked 5' to the nucleic acid sequence encoding the antisense oligonucleotide. Any promoter that is capable of directing initiation of transcription in a eukaryotic cell can be used in the invention. For example, non-tissue specific promoters, such as the cytomegalovirus (DeBernardi et al., Proc. Natl. Acad. Sci. USA 88:9257–9261, 1991, and references therein), mouse metallothionine I gene (Hammer, et al., J. Mol. Appl. Gen. 1:273—288, 1982), HSV thymidine kinase (McKnight, Cell 31:355–365 1982), and SV40 early (Benoist et al., Nature 290:304–310, 1981) promoters can be used. Tissue-specific promoters can also be selected, depending on the type of cell in which expression of the modified snoRNA is desired. Viral promoters and enhancers, such as those from cytomegalovirus, herpes simplex viruses (types I and II), hepatitis viruses (A, B, and C), and Rous sarcoma virus (RSV; Fang et al., Hepatology 10:781–787, 1989), can also be used in the invention.

Recombinant vectors containing nucleic acid sequences encoding modified snoRNAs can be used in therapeutic compositions for, e.g., treating conditions associated with undesired expression of an mRNA (e.g., viral mRNAs, or mRNAs associated with undesired cell growth such as cancer or arteriosclerosis), or for stabilizing ribozymes or antisense molecules introduced by gene therapy. The therapeutic compositions of the invention can be used alone or in admixture, or in chemical combination, with one or more materials, including other recombinant vectors, materials that increase the biological stability of the recombinant vectors, or materials that increase the ability of the therapeutic compositions to specifically penetrate the relevant cell type. The therapeutic compositions of the invention are administered in pharmaceutically acceptable carriers (e.g., physiological saline), which are selected on the basis of the mode and route of administration, and standard pharmaceutical practice. Suitable pharmaceutical carriers, as well as pharmaceutical necessities for use in pharmaceutical formulations, are described in *Remington's Pharmaceutical Sciences*, a standard reference text in this field, and in the USP/NF.

The therapeutic compositions of the invention are administered in dosages determined to be appropriate by one skilled in the art. An appropriate dosage is one that effects a desired result, e.g., a reduction in a symptom of a disease sought to be treated. It is expected that the dosages will vary, depending upon the pharmacokinetic and pharmacodynamic characteristics of the particular agent, and its mode and route of administration, as well as the age, weight, and health of the recipient; the nature and extent of any relevant disease; the frequency and duration of the treatment; the type of, if any, concurrent therapy; and the desired effect. It is expected that a useful dosage contains between about 0.1 to 100 mg of active ingredient per kilogram of body weight. ordinarily, 0.5 to 50 mg, and preferably, 1 to 10 mg of active ingredient per kilogram of body weight per day given in divided doses, or in sustained release form, is appropriate.

The therapeutic compositions of the invention can be administered to a patient by any appropriate mode, e.g., parenterally, intraperitoneally, orally, topically (e.g., with dimethyl sulfoxide (DMSO)), or intravenously, as determined by one skilled in the art. Alternatively, it may by necessary to administer the treatment surgically to the target tissue. The treatments of the invention can be repeated as needed, as determined by one skilled in the art.

The invention also includes any other methods that accomplish in vivo transfer of nucleic acids into eukaryotic cells. For example, nucleic acids encoding snoRNAs (or snoRNAs themselves) can be packaged into liposomes, non-viral nucleic acid-based vectors, erythrocyte ghosts, or microspheres (e.g., microparticles; see, e.g., U.S. Pat. No. 4,789,734; U.S. Pat. No. 4,925,673; U.S. Pat. No. 3,625,214; Gregoriadis, *Drug Carriers in Biology and Medicine*, pp. 287–341 (Academic Press, 1979)). Further, delivery of snoRNAs can be accomplished by direct injection of the snoRNAs into target tissues, for example, in a calcium phosphate precipitate or coupled with lipids.

Exogenously provided snoRNAs can contain modified nucleotides, e.g., modified nucleotides that enhance stability. For example, the snoRNAs can contain inter-nucleotide linkages other than phosphodiester bonds, such as phosphorothioate, methylphosphonate, methylphosphodiester, phosphorodithioate, phosphoramidate, phosphotriester, or phosphate ester linkages (Uhlman et al., Chem. Rev. 90(4):544–584, 1990; Anticancer Research 10:1169, 1990). snoRNA stability can also be increased by incorporating 3'-deoxythymidine or 2'-substituted nucleotides (substituted with, e.g., alkyl groups) into the snoRNAs during synthesis, by providing the snoRNAs as phenylisourea derivatives, or by having other molecules, such as aminoacridine or polylysine, linked to the 3' ends of the snoRNAs (see, e.g., Anticancer Research 10:1169–1182, 1990). Modifications of the RNA nucleotides of the snoRNAs of the invention may be present throughout the snoRNA, or in selected regions, e.g., the 5' and/or 3' ends. The snoRNAs can also be modified to increase their ability to penetrate the target tissue by, e.g., coupling them to lipophilic compounds. The snoRNAs of the invention can be made by standard methods known in the art, including standard chemical synthesis and transcription of DNA encoding them. In addition, snoRNAs can be targeted to particular cells by coupling them to ligands specific for receptors on the cell surface of a target cell. snoRNAs can also be targeted to specific cell types by being conjugated to monoclonal antibodies that specifically bind to cell-type-specific receptors.

In addition to methylating ribonucleotides in the cells of higher eukaryotes, such as humans, the methods of the invention can be used for methylating ribonucleotides in other organisms, such as animals (e.g., cows, dogs, cats, sheep, goats, rabbits, rats, guinea pigs, hamsters, and mice) and plants.

The methods of the invention can also be applied to methylating ribonucleotides in fungi. For example, the invention can be applied in methods for treating a fungal infection (e.g., *Candida albicans, Blastomyces dermatitidus*, and *Histoplasma capsulatum*), in a patient. In these methods, snoRNAs can be targeted to fungal RNA sequences which, when methylated, reduce, e.g., the rate of cell division. For treatment of some of the manifestations of these infections, topical administration may be desired. For topical administration, e.g., a therapeutically effective amount of one or more of nucleic acid constructs encoding a snoRNA of the invention is applied to the desired site on the skin, preferably in combination with a pharmaceutically acceptable carrier, e.g., a spreadable cream, gel, lotion, or ointment, or a liquid such as saline. For use on the skin, the penetration of the snoRNA into the tissue may be accomplished by a variety of methods known to those of ordinary skill in this field. For example, the construct may be applied directly and mechanically rubbed into the skin. Furthermore, the nucleic acid construct may be incorporated into a transdermal patch that is applied to the skin. Preferably, the penetration resulting from these methods is enhanced with a chemical transdermal delivery agent such as dimethyl sulfoxide (DMSO) or the nonionic surfactant, n-decylmethyl sulfoxide (NDMS), as described in Choi et al., Pharmaceutical Res., 7(11):1099, 1990. Dosages for a therapeutically effective amount for topical application would be in the range of 100 ng to 10 mg per treated surface area per day.

OTHER EMBODIMENTS

It is to be understood that, while the invention has been described in conjunction with the detailed description thereof, the foregoing description is intended to illustrate and not limit the scope of the invention. Other aspects, advantages, and modifications of the invention are within the scope of the following claims.

What is claimed is:

1. A method of methylating the 2'-O-hydroxyl group of a target ribonucleotide in a target nucleic acid, the method comprising contacting the target nucleic acid with a modified snoRNA under conditions sufficient for methylation of the target ribonucleotide to occur, wherein the modified snoRNA comprises
  a binding nucleotide sequence that hybridizes to a portion of the target nucleic acid including the target ribonucleotide, and
  a D box sequence located five nucleotides downstream from a nucleotide in the binding nucleotide sequence that base-pairs with the target ribonucleotide;

wherein the nucleotide sequence of the modified snoRNA is altered compared to a nucleotide sequence of an unmodified snoRNA in that the binding nucleotide sequence does not exist in the sequence of the unmodified snoRNA and is added to form the modified snoRNA; and wherein hybridization of the binding nucleotide sequence to said portion results in methylation of the 2'-O-hydroxyl group of the target ribonucleotide.

2. The method of claim 1, wherein the target nucleic acid is in a cell.

3. The method of claim 2, wherein the target nucleic acid is in a nucleus of the cell.

4. The method of claim 2, wherein the target nucleic acid is in a nucleolus of the cell.

5. The method of claim 2, wherein the target nucleic acid is in the cytoplasm of the cell.

6. The method of claim 2, wherein the target nucleic acid is in a mitochondrion of the cell.

7. The method of claim 1, wherein the target nucleic acid is an RNA.

8. The method of claim 7, wherein the target nucleic acid is a ribosomal RNA.

9. The method of claim 7, wherein the target nucleic acid is an mRNA.

10. The method of claim 8, wherein the target nucleic acid is in a cell.

11. The method of claim 1, wherein the target nucleic acid comprises the genome of a pathogen or RNA transcribed from the genome of a pathogen.

12. The method of claim 1, wherein the target ribonucleotide is in an RNA cleavage site.

13. The method of claim 1, wherein the D box consists of a sequence selected from the group consisting of 5'-CUGA-3', 5'-AUGA-3', 5'-CCGA-3', 5'-CAGA-3', 5'-CUUA-3', 5'-UUGG-3', and 5'-CAGC-3'.

14. A modified snoRNA comprising
  a binding nucleotide sequence that hybridizes to a portion of a target nucleic acid including a target ribonucleotide, and
  a D box sequence located five nucleotides downstream from a nucleotide in the binding nucleotide sequence that base-pairs with the target ribonucleotide;

wherein the nucleotide sequence of the modified snoRNA is altered compared to a nucleotide sequence of an unmodified snoRNA in that the binding nucleotide sequence does not exist in the sequence of the unmodified snoRNA and is added to form the modified snoRNA; and wherein the modified snoRNA targets methylation of the 2'-O-hydroxyl group of the target ribonucleotide.

15. The modified snoRNA of claim 14, wherein the target nucleic acid is an RNA.

16. The modified snoRNA of claim 15, wherein the target nucleic acid is an mRNA.

17. The modified snoRNA of claim 15, wherein the target nucleic acid is a ribosomal RNA.

18. The modified snoRNA of claim 14, wherein the target nucleic acid comprises the genome of a pathogen or RNA transcribed from the genome of a pathogen.

19. The modified snoRNA of claim 18, wherein the pathogen is a human immunodeficiency virus.

20. The modified snoRNA of claim 18, wherein the pathogen is a pathogenic fungus.

21. The modified snoRNA of claim 14, wherein the target ribonucleotide is in an RNA cleavage site.

22. The modified snoRNA of claim 14, wherein the D box consists of a sequence selected from the group consisting of 5'-CUGA-3', 5'-AUGA-3', 5'-CCGA-3', 5'-CAGA-3', 5'-CUUA-3', 5'-UUGG-3', and 5'-CAGC-3'.

23. A method of inhibiting growth of a cell, the method comprising obtaining a modified snoRNA of claim 14, wherein the binding nucleotide sequence is designed to hybridize to a portion of a target nucleic acid within the cell; and introducing the modified snoRNA into the cell;

wherein the modified snoRNA methylates the target nucleic acid, thereby inhibiting growth of the cell.

24. The method of claim 23, wherein the target nucleic acid is an mRNA.

25. The method of claim 23, wherein the target nucleic acid is a ribosomal RNA.

26. The method of claim 23, wherein the cell is a tumor cell.

27. The method of claim 23, wherein the cell is a fungal cell.

28. A method of inhibiting viral replication, the method comprising obtaining a modified snoRNA of claim 14, wherein the binding nucleotide sequence is designed to hybridize to a portion of a target nucleic acid generated by a virus; and contacting the virus with the modified snoRNA;

wherein the modified snoRNA methylates the target nucleic acid, thereby inhibiting replication of the virus.

29. The method of claim 1, wherein the unmodified snoRNA is a naturally occurring snoRNA.

30. The modified snoRNA of claim 14, wherein the unmodified snoRNA is a naturally occurring snoRNA.

31. A method of methylating the 2'-O-hydroxyl group of a target ribonucleotide in a target nucleic acid, the method comprising contacting the target nucleic acid with a modified snoRNA under conditions sufficient for methylation of the target ribonucleotide to occur, wherein the modified snoRNA comprises a binding nucleotide sequence that hybridizes to a portion of the target nucleic acid including the target ribonucleotide, and a D box sequence located five nucleotides downstream from a nucleotide in the binding nucleotide sequence that base-pairs with the target ribonucleotide;

wherein the nucleotide sequence of the modified snoRNA is altered compared to a nucleotide sequence of an unmodified snoRNA in that the binding nucleotide sequence in the unmodified snoRNA is in a different location with respect to the D box sequence in the modified snoRNA; and wherein hybridization of the binding nucleotide sequence to said portion results in methylation of the 2'-O-hydroxyl group of the target ribonucleotide.

32. The method of claim 31, wherein the unmodified snoRNA is a naturally occurring snoRNA.

33. A modified snoRNA comprising a binding nucleotide sequence that hybridizes to a portion of a target nucleic acid including a target ribonucleotide, and a D box sequence located five nucleotides downstream from a nucleotide in the binding nucleotide sequence that base-pairs with the target ribonucleotide;

wherein the nucleotide sequence of the modified snoRNA is altered compared to a nucleotide sequence of an unmodified snoRNA in that the binding nucleotide sequence in the unmodified snoRNA is in a different location with respect to the D box sequence in the modified snoRNA; and wherein the modified snoRNA targets methylation of the 2'-O-hydroxyl group of the target ribonucleotide.

34. The modified snoRNA of claim 33, wherein the unmodified snoRNA is a naturally occurring snoRNA.

* * * * *